United States Patent
Haider

(10) Patent No.: US 7,570,051 B2
(45) Date of Patent: Aug. 4, 2009

(54) MR TOMOGRAPHY WITH A SYSTEM FOR CONTRAST OPTIMIZATION OF MRT IMAGES

(75) Inventor: Sultan Haider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 41 days.

(21) Appl. No.: 11/737,188

(22) Filed: Apr. 19, 2007

(65) Prior Publication Data

US 2007/0247157 A1    Oct. 25, 2007

(30) Foreign Application Priority Data

Apr. 20, 2006  (DE) ................. 10 2006 018 413

(51) Int. Cl.
    *G01V 3/00* (2006.01)
(52) U.S. Cl. ............................ 324/307
(58) Field of Classification Search ......... 324/300–322; 600/410–435
    See application file for complete search history.

(56) References Cited

U.S. PATENT DOCUMENTS

| | | | |
|---|---|---|---|
| 4,770,182 A * | 9/1988 | Damadian et al. | 600/410 |
| 5,095,906 A * | 3/1992 | Ema | 600/407 |
| 5,814,991 A | 9/1998 | Deimling | |
| 5,818,231 A * | 10/1998 | Smith | 324/309 |
| 6,574,629 B1 * | 6/2003 | Cooke et al. | 707/10 |
| 6,584,216 B1 * | 6/2003 | Nyul et al. | 382/131 |
| 6,888,350 B2 | 5/2005 | Deimling | |
| 6,904,306 B1 * | 6/2005 | Wu et al. | 600/420 |
| 6,956,373 B1 * | 10/2005 | Brown et al. | 324/309 |
| 7,054,473 B1 * | 5/2006 | Roehrig et al. | 382/128 |
| 7,145,336 B2 * | 12/2006 | Brown | 324/309 |
| 7,203,350 B2 * | 4/2007 | Leichter et al. | 382/128 |
| 7,212,661 B2 * | 5/2007 | Samara et al. | 382/131 |
| 7,236,637 B2 * | 6/2007 | Sirohey et al. | 382/240 |

(Continued)

FOREIGN PATENT DOCUMENTS

WO    WO 2004/095048    11/2004

OTHER PUBLICATIONS

"syngo—der neue Standard für Bildbetrachtungs-und Workstation-Software," Reichert et al, Electromedica vol. 62, No. 2 (1999) pp. 60-63.

(Continued)

*Primary Examiner*—Brij B. Shrivastav
*Assistant Examiner*—Dixomara Vargas
(74) *Attorney, Agent, or Firm*—Schiff Hardin LLP

(57) ABSTRACT

An MR tomography apparatus has a system for contrast optimization of MRT images, with: an input unit for measurement parameters such as, for example, TR, TE, FOV, matrix size, flip angle, . . . etc. a unit for establishment of the anatomical area to be examined in the examination subject; a unit for combination of a plurality of MRT images acquired with various measurement parameters; and a unit for visualization and generation of a DICOM header for selected MRT image combinations. The tomography apparatus also has a storage unit in which predetermined experiential values for parameters of equations for combination of a number of various MRT images are stored with regard to a number of selectable anatomical areas of an examination subject; and an acquisition unit for generation of MRT images under selective consideration of the experiential values for measurement parameters that are stored for the anatomical structure to be examined.

9 Claims, 1 Drawing Sheet

U.S. PATENT DOCUMENTS

| | | | |
|---|---|---|---|
| 7,412,279 B2 * | 8/2008 | Weisskoff et al. | 600/420 |
| 7,418,119 B2 * | 8/2008 | Leichter et al. | 382/128 |
| 7,421,136 B2 * | 9/2008 | Sirohey et al. | 382/240 |
| 2002/0183612 A1 | 12/2002 | Deimling | |
| 2004/0082846 A1 * | 4/2004 | Johnson et al. | 600/410 |
| 2005/0154292 A1 * | 7/2005 | Tank | 600/410 |
| 2006/0264763 A1 | 11/2006 | Deimling et al. | |
| 2007/0022377 A1 | 1/2007 | Haider et al. | |

OTHER PUBLICATIONS

Method for Predicting Imaging Equipment, Region of Interests and Measurement Parameters for Follow-up Morphologic Staging of Pathological Findings for Whole Body Examination s(MRI, CT, PET, US etc.), Haider et al, Technology Report at www.ip.com, Sep. 20, 2005, vol. 99.

* cited by examiner

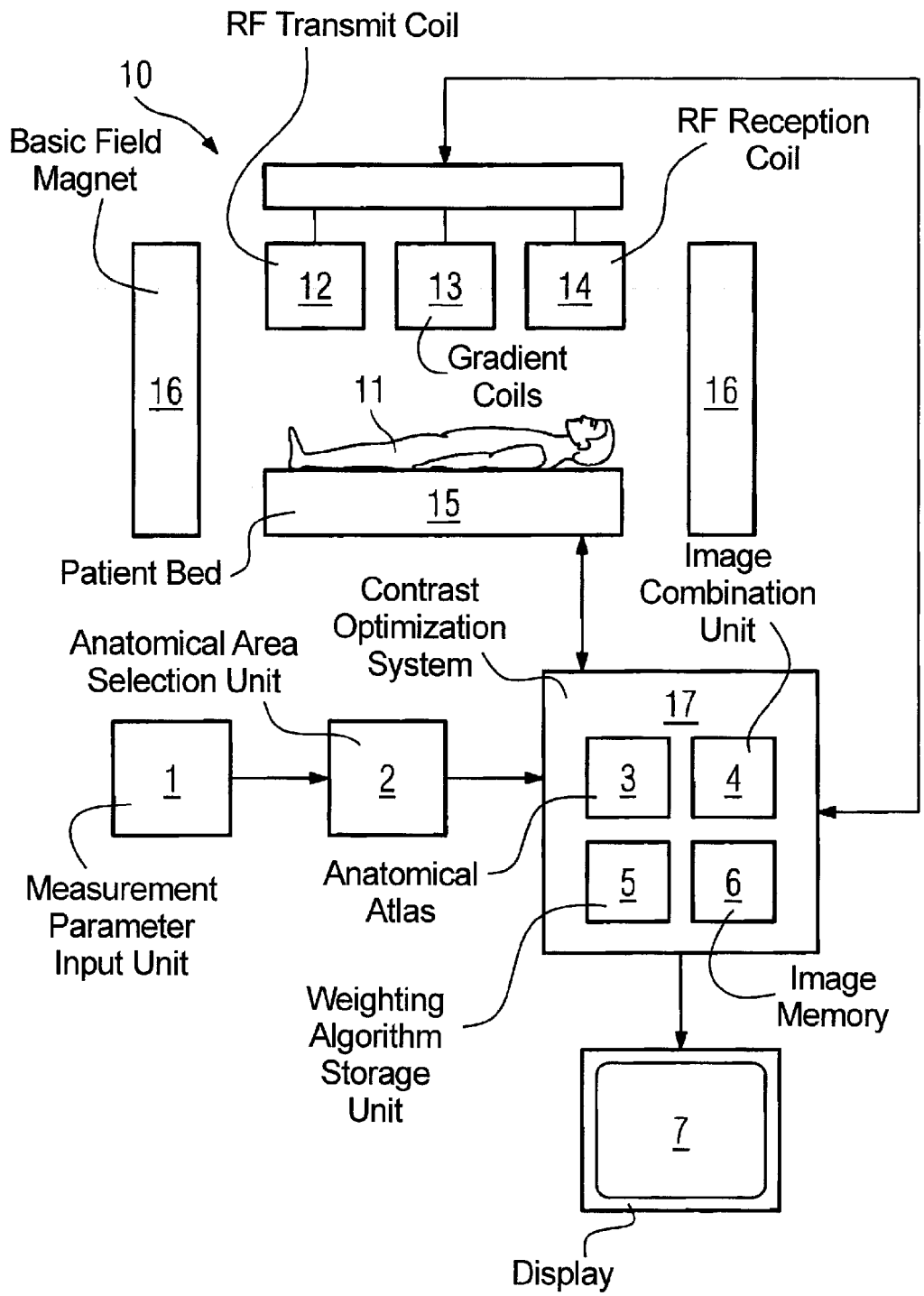

MR TOMOGRAPHY WITH A SYSTEM FOR CONTRAST OPTIMIZATION OF MRT IMAGES

BACKGROUND OF THE INVENTION

1. Field of the Invention

The present invention concerns an MR tomography with a system for contrast optimization of MRT.

2. Description of the Prior Art

Magnetic resonance tomography (MRT) enables the non-invasive acquisition of measurement data of a patient and processing the acquired measurement data into high-contrast images that are used in medical diagnostics. Various pulse sequences are available for MR imaging that differ due to the different type of the echo generation (spin echo, gradient echo) and the adjustment of the relevant measurement parameters (such as the repetition time $T_R$ and the echo time $T_E$ of the flip angle $\alpha$ etc.) within a selected pulse sequence.

Tissue-specific parameters are the spin-grid relaxation time $T_1$ and the spin-spin relaxation time $T_2$ as well as the proton density PD. Based on the tissue-dependent specification of these parameters, it is possible to image tissue with different contrast in an MR image via suitable selection of the repetition time TR and the echo time TE. Depending on the selection of $T_R$ and $T_E$, $T_1$-weighted, $T_2$-weighted or proton-weighted MR images can be acquired. Which of these weightings is the most suitable (i.e. delivers the most high-contrast MR image) depends on the diagnostic goal, in particular on the type of the examined tissue.

The contrast can additionally be influenced by the application of contrast agent or by preparation of the magnetization, such as through MTC (magnetization transfer contrast).

Examples for pulse sequences that differ with regard to the contrast of the obtainable MR images, or within which the MR image contrast can be varied significantly by variation of the measurement parameters $T_R$, $T_E$ and $\alpha$, are the HASTE sequence, the TrueFISP sequence, the DESS sequence, the CISS sequence and the SINOP sequence. Depending on the selection of the above parameters, $T_1$- or $T_2$-weighted MR images are obtained in which watery structures or fatty structures are shown brightly contrasting.

The HASTE sequence delivers a weakly $T_2$-weighted MR image for a relatively small effective echo time $T_{eff}$, i.e. for a short temporal interval between the excitation pulse and the echo in which the phase coding gradient has the smallest amplitude, while $T_2$-weighted MR images are obtained for a long effective echo time $T_{eff}$. The multi-echo HASTE sequence enables the acquisition of MR images with varying contrast. With regard to the contrast of different MR images, these can be further used for the generation of a combination image that exhibits a better contrast in an anatomical region of interest.

Gradient echo sequences lead to mixed contrasts. The TrueFISP sequence thus delivers a typical $T_2/T_1$ contrast. The cerebrospinal fluid is shown very bright while tissue (such as white or grey brain matter) appears only with weak signal in the MR image. The DESS sequence comprises the simultaneous acquisition of an MR image on the basis of the aforementioned FISP sequence and on the basis of a further MR image using the PSIF sequence, which (presented in a simplified manner) represents a reversal of the TrueFISP sequence. While the FISP sequence shows the typical $T_2/T_1$ contrast, the PSIF MR image is strongly $T_2$-weighted. An MR image with particularly high brightness in the region of cerebrospinal fluid is acquired via the subsequent addition of the magnitudes of the images in the framework of the DESS method, i.e. the addition of the signal intensities of pixels at the same location. The 3D DESS method is therefore primarily used for orthopedic imaging, for example for the differentiation of cartilage and fluid.

The CISS sequence includes two successive 3D b-SSFP passes and is thus likewise based on the TrueFISP sequence. Two image data sets are acquired whose "banding" artifacts are displaced counter to one another. The "banding-free" CISS image is obtained via "maximum intensity projection" or a special algorithm for combination of these two image data sets.

It is known to add or to subtract two congruent images generated in the same manner, i.e. images that image the same section in the examination subject. For each image point the magnitude (absolute) value of the associated image point of the second image is added to or subtracted from a magnitude value of an image point of a first image. An existing contrast can be intensified (amplified) in this manner, or new contrasts can be generated. Moreover, the image addition or the image subtraction offers the possibility to avoid image artifacts. The CISS sequence is implemented with the goal of the avoiding of such artifacts.

The post-processing of measurement data (such as raw data or image data) occurs using known algorithms such as, for example, the sum-of-squares algorithm.

Image subtraction for this purpose is known, for example, from DE 196 16 387 A1. A further method for image generation is described in DE 101 21 802 A1 (corresponding to United States Application Publication No. 2002/0183612 A1). These latter, corresponding publications disclose a magnetic resonance tomography apparatus having a system for contrast optimization of MRT images, having an input unit for measuring parameters such as, for example, TR, TE, FOV, matrix size, flip angle, etc., a unit for establishing the anatomical area in the examination subject to be examined, a unit for combining a number of MRT images acquired with various measurement parameters, and a unit for visualization and generation of a DICOM header for selected MRT image combinations.

DE 196 16 387 A1 concerns what is known as the HIRE method ("High Intensity Reduction Sequence"). After an excitation, two groups of nuclear magnetic resonance signals are acquired in two time spans with varying interval for excitation. The image is acquired via subtraction of the nuclear magnetic resonance signals of the first and the second group with respectively coinciding spatial coding.

DE 101 21 802 A1 concerns a method for image generation that comprises the generation of a first image matrix and of a second image matrix and the addition or subtraction of the magnitude values of the image points with the same spatial coding in both image matrices. In this method the magnitude values of the image points are weighted dependent on the local image conditions, with the image points usable for an improvement of the image quality being filtered out. This method for image post-processing is applied to image matrices that were acquired according to the aforementioned HIRE method or the DESS method.

In WO 2004/095048 A1 a method for generation of a magnetic resonance image is disclosed in which a number of echo signals are acquired with at least two different echo time values. The echo signals of each time value are then processed into an intermediate image, after which an analysis of the intermediate image and the ultimate combination into a total image follow.

The possibilities described above for contrast improvement, contrast generation and avoidance of artifacts in MR images represent a considerable enrichment of MR technology. At the same time, however, they also place ever greater demands on the user because an increasing, unmanageable number of parameters must be taken into account to solve presented tasks, such as the high-contrast or contrast-intensified imaging of a body region and the achievement of the contrast optimal for the diagnostic use. The correct adjustment of these parameters can increasingly only be effected by highly qualified technicians. Moreover, measurements in a magnetic resonance tomograph are relatively costly, such that in the application case it is not possible to achieve the desired result iteratively under implementation of a plurality of preliminary tests on a patient. The implementation of such preliminary tests is also precluded if the patient (as often occurs) is not able or willing to remain motionless for longer times in a magnetic resonance tomography scanner.

The introduction of imaging systems into the clinical routine is assisted by flexible software that is user-friendly. The SYNGO® platform (registered trademark of the Siemens Corporation) represents such software with a user-friendly user interface (Reichert T., Herget M., "SYNGO—The new standard for viewing and workstation software"; electromedica, 1999, 67(2): p. 60-63).

SUMMARY OF THE INVENTION

An object of the present invention is to provide an MR tomography apparatus with a system for contrast optimization of MRT images that enables an optimized selection of measurement parameters and combinations of MR images such that MR images with improved contrast or new contrast, with reduced image artifacts can be obtained, with a shorter duration of the measurement (data acquisition). The application costs thus can be reduced. Moreover, the acceptance (comfort level) of the patient should be improved with regard to the implementation of measurements in a nuclear magnetic resonance tomography scanner.

The above object is achieved in accordance with the present invention in a magnetic resonance tomography apparatus having a system for contrast optimization of MRT images having an input unit that allows measurement parameters to be entered, a unit that establishes the anatomical area of the examination subject that is to be examiner, a unit for combining a number of MRT images acquired with measurement parameters, a unit for visualization and generation of a DICOM (Digital Imaging and Communications in Medicine) header for selected MRT image combinations, a storage unit in which predetermined experimental values for equation parameters for combining multiple MRT images are stored, with regard to a number of selectable anatomical areas of the examination subject, and a magnetic resonance data acquisition unit that is operated according to the aforementioned parameters that are associated with the anatomical structure to be examined.

The inventive MR tomography apparatus allows an excellent visualization of fluid-containing structures and of lesions. The inventive technique has the following clinical advantages: the possibility of the characterization of focal liver lesions; detection of acute pancreatitis, acute cholecystitis, biliary fistula, the slight anomalies of the bile duct and of the pancreatic channel; and differentiation between acute and chronic cholecystitis.

DESCRIPTION OF THE DRAWING

The single figure is a schematic block diagram of a magnetic resonance imaging apparatus constructed and operating in accordance with the principles of the present invention.

DESCRIPTION OF THE PREFERRED EMBODIMENTS

The inventive MR tomograph has in a known manner, an input unit 1 for measurement parameters. Such measurement parameters are, among other things, the repetition time (TR), the echo time (TE), the image field (FOV), the matrix size, the number of the slices, and the flip angle. Techniques for improving image quality can also possibly be input as well, such as, for example, the use of contrast agents.

The tomograph also has a unit 2 for establishment of the anatomical area to be examined in the examination subject. The examination subject is normally a patient 11 and the anatomical area is normally a slice perpendicular to the longitudinal axis of the patient lying in the scanner tube, or a sagittal slice or a coronary slice, the latter two slices lying in respective planes parallel to the longitudinal axis of the patient.

The tomography apparatus inventively has a system 17 for contrast optimization that includes a storage unit 3 in which is stored a "look-up table" or an "anatomical atlas". Stored in this storage unit 3 (called "atlas" for short in the following) are predetermined measurement parameter values for every selectable slice region, i.e. for every anatomical region to be examined. These were empirically detected in comparable examination subjects and reflect experiential values given whose previous use optimal, high-contrast MR images have been generated.

These are either automatically taken into account for the following acquisitions of MR images or are offered to the operator as setting options. The operator can adopt the proposed values or replace them with values the operator selects himself or herself.

The inventive system 17 also includes a unit 4 for combination of a number of MR images acquired with various measurement parameters. For example, a number of images can be combined with one another by subtraction and/or addition methods such that optimal contrast ratios predominate in the regions of interest to the operator. These do not have to be linear addition or subtraction processes; the use of weightings is conceivable that follow empirically-determined algorithms that are likewise stored in storage units and are generated in the image processing.

The atlas is updated after each concluded generation of an MR image which satisfies the operator with regard to the achieved contrast. This means that the previous parameter values used and stored there are replaced by current parameter values. The system is thereby self-teaching and optimizes itself alone over time. The image satisfying the operator is visualized and stored in an image memory 6 and a "DICOM header" is generated for selected MRT image combinations.

The measurement parameter selection is made by the operator dependent on the pathological finding to be expected. The same applies for the selection of the combination of the MR images to be combined.

If the contrast optimization of the system results in only unsatisfactory contrast values, the system thus proposes the additional use of contrast agents to the operator.

Known pattern recognition programs are used in the determination of optimal measurement parameter values such as, for example, the $T_1$, $T_2$ or PD weightings.

A proven combination of various MR images is the acquisition of an MR image with weakly-weighted $T_2$ value and the acquisition of an image with strongly-weighted $T_2$ value in the HASTE technique, these images being subsequently added to one another or, respectively, subtracted from one another.

A further combination is the addition or subtraction of images that are acquired once "in phase" and once with "opposite phase". The individual image values of individual images can thereby be weighted with a factor before the addition or subtraction. If the result of this image combination is furthermore unsatisfactory due to weak contrast, the system proposes the use of specific filters that are stored in a filter databank of the system.

In follow-up examinations of the same examination subject, given significant deviation of optimal measurement parameters the system can also indicate pathological changes associated with this deviation.

Given the overlap of various MR images, whose contours do not always have to coincide one hundred percent (for example because the patient executes breathing movements or does not lie in the exact same position in the tomograph in follow-up examinations), known CAD methods and a standardized anatomical coordinate system are used for superimposition.

After a concluded examination and selection of an optimal MR image, the system automatically generates an acquisition protocol in which the measurement parameters are adhered to as well as a "post-processing protocol" in which the individual steps of the image combinations are adhered to. A "DICOM header" is then generated with these data such that the ultimately acquired MR exposure can be stored as a component of an electronic patient report or diagnosis report.

A magnetic resonance data acquisition unit 10 is operated according to the aforementioned measurement parameter values. The hardware of the magnetic resonance data acquisition unit 10 is conventional, but the data acquisition unit 10 is controlled (operated) in accordance with the present invention. The data acquisition unit 10 therefore includes an RF transmit coil 12, a number of gradient coils 13, and an RF reception coil 14. As is known, the same RF coil (or coil array) can be used as the RF transmit coil 12 and the RF reception coil 15.

The patient 11 on a patient bed 15 is within a static basic magnetic field, generated by a basic field magnet 16.

The inventive MR tomograph thus enables the operator MR to acquire MR images with improved contrast given simultaneously shorter duration of the measurement, whereby the application costs are reduced and the residence duration of a patient in the tomograph tube is reduced, which increases the patient's acceptance of such an examination.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic resonance tomography apparatus comprising:
    an input unit allowing entry of measurement parameters for acquiring magnetic resonance image data;
    a unit allowing selection of an anatomical area of an examination subject to be examined using said measurement parameters;
    a unit that combines a plurality of magnetic resonance images acquired with respectively different measurement parameters;
    a storage unit containing predetermined experimental values for equation parameters for combining said plurality of MR images for respectively different anatomical areas of an examination subject;
    a magnetic resonance data acquisition unit that is controlled, to acquire magnetic resonance data from the subject, using measurement parameters associated with the combination of said plurality of MR images dependent on the selected anatomical area; and
    a unit that generates a DICOM header for the combination of said plurality of said MR images and a visualization unit for said combination; and in that said plurality of MR images are combined as exposures with weakly-weighted $T_2$ values acquired with a HASTE technique.

2. A magnetic resonance tomography apparatus as claimed in claim 1 comprising an updating unit that updates a content of the storage unit for the selected anatomical area with measurement parameters that produce an optimal contrast in a previous image acquisition.

3. A magnetic resonance tomography apparatus as claimed in claim 2 wherein said unit for combining said plurality of MR images combines said plurality of MR images dependent on pathological findings that are entered into said unit.

4. A magnetic resonance tomography apparatus as claimed in claim 1 wherein said apparatus provides a prompt to said operator, at said display to administer a contrast agent if a contrast valued is determined to be unsatisfactorily low after optimization of the contrast.

5. A magnetic resonance tomography apparatus as claimed in claim 1 including a pattern recognition unit that determines optimal measurement parameter values for weighting said plurality of MR images in said combination.

6. A magnetic resonance tomography apparatus comprising:
    an input unit allowing entry of measurement parameters for acquiring magnetic resonance image data;
    a unit allowing selection of an anatomical area of an examination subject to be examined using said measurement parameters;
    a unit that combines a plurality of magnetic resonance images acquired with respectively different measurement parameters;
    a storage unit containing predetermined experimental values for equation parameters for combining said plurality of MR images for respectively different anatomical areas of an examination subject;
    a magnetic resonance data acquisition unit that is controlled, to acquire magnetic resonance data from the subject, using measurement parameters associated with the combination of said plurality of MR images dependent on the selected anatomical area; and
    a unit that generates a DICOM header for the combination of said plurality of said MR images and a visualization unit for said combination, and in that said unit that combines said plurality of MR images combines images acquired in phase and images acquired with an opposite phase with one another.

7. A magnetic resonance tomography apparatus comprising:
    an input unit allowing entry of measurement parameters for acquiring magnetic resonance image data;
    a unit allowing selection of an anatomical area of an examination subject to be examined using said measurement parameters;
    a unit that combines a plurality of magnetic resonance images acquired with respectively different measurement parameters;
    a storage unit containing predetermined experimental values for equation parameters for combining said plurality of MR images for respectively different anatomical areas of an examination subject;
    a magnetic resonance data acquisition unit that is controlled, to acquire magnetic resonance data from the subject, using measurement parameters associated with the combination of said plurality of MR images dependent on the selected anatomical area; and a unit that generates a DICOM header for the combination of said plurality of said MR images and a visualization unit for said combination, and in that said apparatus provides a prompt at said display to employ an electronic filter, stored in an electronic filter data bank, upon a determination of an unsatisfactorily low contrast value after contrast optimization.

8. A magnetic resonance tomography apparatus comprising:

an input unit allowing entry of measurement parameters for acquiring magnetic resonance image data;

a unit allowing selection of an anatomical area of an examination subject to be examined using said measurement parameters;

a unit that combines a plurality of magnetic resonance images acquired with respectively different measurement parameters;

a storage unit containing predetermined experimental values for equation parameters for combining said plurality of MR images for respectively different anatomical areas of an examination subject;

a magnetic resonance data acquisition unit that is controlled, to acquire magnetic resonance data from the subject, using measurement parameters associated with the combination of said plurality of MR images dependent on the selected anatomical area; and a unit that generates a DICOM header for the combination of said plurality of said MR images and a visualization unit for said combination, and by an updating unit that updates a content of the storage unit for the selected anatomical area with measurement parameters that produce an optimal contrast in a previous image acquisition, and wherein said system indicates correlated pathological changes upon significant changes of measurement parameters after updating said measurement parameters.

9. A magnetic resonance tomography apparatus comprising:

an input unit allowing entry of measurement parameters for acquiring magnetic resonance image data;

a unit allowing selection of an anatomical area of an examination subject to be examined using said measurement parameters;

a unit that combines a plurality of magnetic resonance images acquired with respectively different measurement parameters;

a storage unit containing predetermined experimental values for equation parameters for combining said plurality of MR images for respectively different anatomical areas of an examination subject;

a magnetic resonance data acquisition unit that is controlled, to acquire magnetic resonance data from the subject, using measurement parameters associated with the combination of said plurality of MR images dependent on the selected anatomical area; and a unit that generates a DICOM header for the combination of said plurality of said MR images and a visualization unit for said combination, comprising a CAD technique and a standardized anatomical coordinate system for optimizing the combination of a plurality of MR images.

\* \* \* \* \*